United States Patent
Inanaga et al.

(10) Patent No.: US 6,878,835 B2
(45) Date of Patent: Apr. 12, 2005

(54) CATALYST FOR ASYMMETRIC EPOXIDATION OF ENONES AND PROCESS FOR PRODUCING OPTICALLY ACTIVE EPOXIDE EMPLOYING IT

(75) Inventors: Junji Inanaga, Fukuoka (JP); Takumi Kagawa, Shinnanyo (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 10/714,599

(22) Filed: Nov. 18, 2003

(65) Prior Publication Data

US 2004/0116721 A1 Jun. 17, 2004

Related U.S. Application Data

(62) Division of application No. 09/788,371, filed on Feb. 21, 2001, now Pat. No. 6,680,275.

(30) Foreign Application Priority Data

Feb. 23, 2000 (JP) ...................................... 2000-052148
Mar. 13, 2000 (JP) ...................................... 2000-073996

(51) Int. Cl.$^7$ .......................... C07D 303/00; B01J 31/00
(52) U.S. Cl. ...................................... 549/513; 502/162
(58) Field of Search .......................... 549/513; 502/162

(56) References Cited

U.S. PATENT DOCUMENTS

| | | | |
|---|---|---|---|
| 5,336,653 A | 8/1994 | Shibasaki et al. | |
| 6,201,123 B1 | 3/2001 | Daikai et al. | |
| 2001/0051737 A1 | 12/2001 | Inagana et al. | ............. 502/160 |
| 2002/0039961 A1 | 4/2002 | Shibasaki | ................... 502/171 |

FOREIGN PATENT DOCUMENTS

| JP | 10 120668 A | 5/1998 |
|---|---|---|
| JP | 2000 229242 | 8/2000 |

OTHER PUBLICATIONS

Daikai et al, "Remarkable Ligand Effect on the Enantioselectivity of the Chiral Lanthanum Complex–Catalyzed Asymmetric Epoxidation of Enones", Tetrahedron Letters, NL, Elsevier Science Publishers, Amsterdam, vol. 39, No. 40, Oct. 1, 1998, pp. 7321–7322, XP004133670.
Bougauchi et al, "Catalytic asymmetric epoxidation of alpha, beta–unsaturated ketones promoted by lanthanoid complexes", Journal of the American Chemical Society, vol. 119, No. 9, Mar. 5, 1997, pp. 2329–2330, XP002170251.
Patent Abstracts of Japan, vol. 1998, No. 10, Aug. 31, 1998 & JP 10 120668 A, May 12, 1998.
Patent Abstracts of Japan, vol. 2000, No. 11, Jan. 3, 2001 & JP 2000 229242 A, Aug. 22, 2000.
Daikai et al, "Evaluation of Chiral Lanthanoid Metal Catalysts Bearing 6,6–disubstituted 1,1'binaphthoxy ligands for the asymmetric epoxidation of enones", Chemical Abstracts, vol. 129, No. 24, Dec. 14, 1998, Abstract No. 316095.
Daikai et al, "Remarkable Ligand Effect on the Enantioselectivity of the Chiral Lanthanum Complex–Catalyzed Asymmetric Epoxidation of Enones", Tetrahedron Letters, NL, Elsevier Science Publishers, Amsterdam, vol. 39, No. 40, Oct. 1, 1998; ISSN: 0040–4039.
Patent Abstracts of Japan, vol. 1998, No. 10, Aug. 31, 1998 & JP 10 120668 A, May 12, 1998 abstract.
Bougauchi et al, "Catalytic asymmetric epoxidation of alpha, beta–unsaturated ketones promoted by lanthanoid complexes", Journal of American Chemical Society, vol. 119, No. 9, Mar. 5, 1997, pp. 2329–2330, XP002170251.
Patent Abstracts of Japan vol. 2000, No. 11, Jan. 3, 2001 & JP 2000 229242 A, Aug. 22, 2000 abstract.

*Primary Examiner*—Cecilia J. Tsang
*Assistant Examiner*—Raymond Covington
(74) *Attorney, Agent, or Firm*—Nixon & Vanderhye P.C.

(57) ABSTRACT

A complex catalyst for asymmetric epoxidation of enones, containing an optically active binaphthol, lanthanum triisopropoxide, triphenylphosphine oxide substituted with electron withdrawing groups in the parapositions of the phenyl groups, and cumene hydroperoxide or tert-butyl hydroperoxide.

4 Claims, No Drawings

CATALYST FOR ASYMMETRIC EPOXIDATION OF ENONES AND PROCESS FOR PRODUCING OPTICALLY ACTIVE EPOXIDE EMPLOYING IT

This application is a divisional of application Ser. No. 09/788,371 filed Feb. 21, 2001, now U.S. Pat. No. 6,680,275.

The present invention relates to a catalyst for asymmetric epoxidation of enones and a process for producing an optically active epoxide employing it.

As a reaction for asymmetric epoxidation of enones, a method has been known wherein a compound having a carbon-carbon double bond conjugated to a carbonyl group, such as chalcone, is asymmetrically epoxidized with a hydroxyperoxide compound in the presence of a complex catalyst prepared from an optically active dihydroxy compound and a rare earth metal alkoxide.

Specifically, it is known to use a tetrahydrofuran solution of (R)-binaphthol and lanthanum triisopropoxide, as a (R)-lanthanum binaphthoxide, for the asymmetric epoxidation reaction (JP-A-10-120668).

However, by the method disclosed in JP-A-10-120668, if, for example, tert-butyl hydroperoxide (hereinafter referred to simply as TBHP) is used as an oxidizing agent, the desired optically active epoxide is obtainable only in a low yield and with a low optical purity. Therefore, in order to obtain a satisfactory result, it has been required to use a special binaphthol having methylol introduced at the 3-position, or to use an alkoxide of a rare earth metal other than lanthanum, such as ytterbium. Further, the amount of the catalyst is required to be from 5 to 10 mol % relative to the enone subjected to the reaction, and reduction of the amount of the catalyst has been desired.

The present applicants have already filed a patent application (JP-10-192743) for a catalyst composition comprising (A) an optically active binaphthol, (B) lanthanum triisopropoxide, (C) triphenylphosphine oxide, etc., which has a higher reactivity than the above-mentioned conventional catalyst and which presents a high optical purity to the product.

The present inventors have conducted a further study on a catalyst which presents a high optical activity and as a result, have found that a complex catalyst comprising (A) an optically active binaphthol, (B) lanthanum triisopropoxide, (C) triphenylphosphine oxide and (D) cumene hydroperoxide or tert-butyl hydroperoxide, is a catalyst which presents a higher optical activity to the product.

Further, the present inventors have conducted an extensive study to develop a catalyst which has a high reactivity and which presents a high optical purity and have found that a catalyst composition comprising (A) an optically active binaphthol, (B) lanthanum triisopropoxide and (c) tri(4-fluorophenyl)phosphine oxide, tri(4-chlorophenyl)phosphine oxide or tri(4-trifluoromethylphenyl)phosphine oxide, has a high reactivity and high stability as compared with the conventional catalyst and presents a high optical purity to the product, and further, it is thereby possible to reduce the amount of the catalyst relative to the enone subjected to the reaction. The present invention has been accomplished on the basis of these discoveries.

Namely, the present invention provides a complex catalyst for asymmetric epoxidation of enones, which comprises:
(A) an optically active binaphthol,
(B) lanthanum triisopropoxide,
(C) triphenylphosphine oxide, and
(D) cumene hydroperoxide or tert-butyl hydroperoxide; a catalyst for asymmetric epoxidation of enones, which comprises:
(A) an optically active binaphthol,
(B) lanthanum triisopropoxide, and
(c) tri(4-fluorophenyl)phosphine oxide, tri(4-chlorophenyl)phosphine oxide or tri(4-trifluoromethylphenyl)phosphine oxide; and a process for producing an optically active epoxide of the following formula (1):

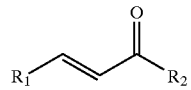

(1)

wherein each of $R_1$ and $R_2$ which are independent of each other, is a $C_{1\text{-}20}$ linear, branched or cyclic alkyl group, an aromatic group, an aromatic group substituted by from 1 to 5 $C_{1\text{-}5}$ alkyl groups, an aromatic group substituted by from 1 to 5 $C_{1\text{-}5}$ alkoxy groups, an aromatic group substituted by from 1 to 5 halogen atoms, a $C_{1\text{-}5}$ linear, branched or cyclic alkyl group substituted by an aromatic group, or a $C_{1\text{-}5}$ linear, branched or cyclic alkyl group substituted by a halogenated aromatic group, and symbol * represents optically active carbon, which comprises reacting an enone of the following formula (2):

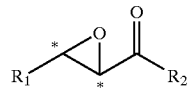

(2)

wherein $R_1$ and $R_2$ are as defined above, with an oxidizing agent in the presence of a such a catalyst.

Now, the present invention will be described in detail with reference to the preferred embodiments.

Firstly, the complex catalyst comprising (A) an optically active binaphthol, (B) lanthanum triisopropoxide, (C) triphenylphosphine oxide and (D) tert-butyl hydroperoxide or cumene hydroperoxide, will be described.

In the present invention, the constituting proportions of the above catalyst components are not particularly limited. However, (A) the binaphthol is usually from 1 to 3 mols, (C) the triphenylphosphine oxide is usually from 0.1 to 10 mols, preferably from 1 to 10 mols, and (D) the tert-butyl hydroperoxide or cumene hydroperoxide is usually from 1 to 20 mols, preferably from 1 to 10 mols, per mol of (B) the lanthanum triisopropoxide.

The above-mentioned components constituting the catalyst are added to a solvent which will be described hereinafter and maintained for from 0.5 to 4 hours within a range of from −50 to 100° C., whereby a complex will be formed. By the formation of the complex, the solution will have a color of yellowish green to deep green.

In the present invention, it is preferred that a solution of the above catalyst complex is preliminarily prepared in the reaction system, and then the substrate to be subjected to the reaction and a necessary amount of an oxidizing agent are added to carry out the reaction.

In a case where the preparation of a solution of the catalyst complex of the present invention is not carried out, for example, in a case where (A) the optically active binaphthol, (B) the lanthanum triisopropoxide and (C) the triphenylphosphine oxide are mixed in a solvent without adding (D) the tert-butyl hydroperoxide or cumene hydroperoxide, and then the substrate to be subjected to the reaction and (D) the tert-butyl hydroperoxide or cumene peroxide are all together added to the system to carry out the reaction, it is likely that the yield will decrease, and the optical purity will decrease.

Now, the catalyst comprising (A) an optically active binaphthol, (B) lanthanum triisopropoxide and (c) tri(4-fluorophenyl)phosphine oxide, tri(4-chlorophenyl)phosphine oxide or tri(4-trifluoromethylphenyl)phosphine oxide, will be described.

In the present invention, the optically active binaphthol is specifically (R)-(+)-1,1'-bi-2-naphthol (hereinafter referred to as (R)-binaphthol) or (S)-(−)-1,1'-bi-2-naphthol (hereinafter referred to as (S)-binaphthol).

In the present invention, the constituting proportions of the above catalyst components are not particularly limited. However, (A) the binaphthol is usually from 1 to 3 mols, and (c) the tri(4-fluorophenyl) phosphine oxide, tri(4-chlorophenyl)phosphine oxide or tri(4-trifluoromethylphenyl)phosphine oxide, is usually from 0.1 to 10 mols, preferably from 1 to 10 mols, per mol of (B) the lanthanum triisopropoxide.

In the present invention, to the above catalyst, a predetermined amount of cumene peroxide (hereinafter sometimes referred to as CMHP) or tert-butyl hydroperoxide (hereinafter sometimes referred to as TBHP) may be added to form a complex showing a yellowish green to deep green color as a reactive species, and the mixture may be used for the reaction. However, in such a case, there is no substantial difference in the obtainable results. Further, to the above catalyst, CMHP or TBHP required for the reaction is preliminarily added, and then the enone may be added to carry out the reaction. However, also in this case, there is no substantial difference in the obtainable results.

In the present invention, the above-mentioned components constituting the catalyst may be added to a solvent which will be described hereinafter and maintained for from 0.5 to 4 hours within a range of from −50° C. to 100° C. to form a complex and then the substrate to be subjected to the reaction and an oxidizing agent may be added to carry out the reaction. Otherwise, a predetermined amount of an oxidizing agent is added to the formed complex, followed by stirring and then an additional oxidizing agent and the enone to be subjected to the reaction may be added to carry out the reaction.

The complex catalyst of the present invention is useful for a reaction for asymmetric epoxidation of enones, and it provides a high reactivity and presents a high optical purity to the product.

The optical absolute configuration to be developed by the reaction employing the complex catalyst of the present invention generally depends on the optical absolute configuration of the optically active binaphthol constituting the catalyst. Namely, with a substrate whereby the absolute configuration of the asymmetric carbon in the product becomes a (R) form when (R)-binaphthol is employed, the optical absolute configuration of the asymmetric carbon in the product will be a (S) form when (S)-binaphthol is employed. However, it is not always true that when (R)-binaphthol is employed, the optical absolute configuration of an asymmetric carbon in the product will be a (R) form, and the optical absolute configuration of the product varies depending upon the type of the substrate. In a case where an asymmetric epoxidation reaction is carried out by means of the catalyst of the present invention, when (R)-binaphthol is employed, the optical absolute configurations at the 2-position (α-position of carbonyl group) and 3-position (β-position of carbonyl group) of the epoxide of the enone, thereby formed, will usually be (2S, 3R), while when (S)-binaphthol is employed, the optical absolute configuration will usually be (2R, 3S).

In the process of the present invention, the amount of the complex catalyst is not particularly limited, but it is usually from 0.01 to 50 mol %, preferably from 0.1 to 25 mol %, based on the molar amount of the lanthanum isopropoxide, relative to the substrate to be subjected to the reaction.

As a solvent useful for the process of the present invention, any solvent may be used so long as it is a solvent inert to the catalyst and to the epoxidation reaction. However, an ether type solvent such as dimethyl ether, diisopropyl ether, 1,2-dimethoxyethane or tetrahydrofuran (hereinafter referred to simply as THF) is preferred from the viewpoint of the stability of the catalyst and the result of the epoxidation reaction, and among them, THF gives the best result.

The amount of the solvent is usually from 2 to 200 times, preferably from 5 to 100 times, by weight, the amount of the enone to be subjected to the reaction.

The enone useful for the process of the present invention may be any enone so long as it is a compound of the above formula (1). Specifically, methyl vinyl ketone, trans-3-penten-2-one, trans-3-hexen-2-one, trans-3-hepten-2-one, trans-3-octen-2-one, trans-3-nonen-2-one, ethyl vinyl ketone, trans-4-hexen-3-one, trans-4-hepten-3-one, trans-4-octen-3-one, trans-4-nonen-3-one, isopropyl vinyl ketone, trans-2-methyl-4-hexen-3-one, trans-2-methyl-4-hepten-3-one, trans-2-methyl-4-octen-3-one, trans-2-methyl-4-nonen-3-one, trans-1,3-diphenyl-2-propylen-1-one (chalcone), trans-2-methyl-5-phenyl-4-penten-3-one, 4-methyl-1-phenyl-3-penten-2-one, 4-phenyl-3-butylen-2-one, 6-phenyl-3-hexen-2-one or 5-phenyl-3-hexen-2-one, may be mentioned.

The oxidizing agent to be used in the present invention is usually CMHP or TBHP. However, other oxidizing agents may be used which have oxidizing powers of an equal level and which bring about no side reactions in the reaction system.

As TBHP to be used as an oxidizing agent in the process of the present invention, a commercially available solution in e.g. decane may be used as it is, or it may be extracted from a 70% or 90% aqueous solution with toluene, then dried over anhydrous magnesium sulfate and then used for the present invention. Likewise, as CMHP, a commercial 80 wt % product may be used after purification or as it is without purification. Further, depending upon the type of the substrate for the reaction, substantially quantitatively, a pure optically active substance can be obtained by using CMHP.

The amount of the oxidizing agent should theoretically be sufficient with an equivalent amount to the enone to be subjected to the reaction in the total of the amount used for the formation of the catalyst and the amount to be added during the reaction. However, to complete the reaction, it is preferably used in an amount of 1.1 times by mol.

In the process of the present invention, if the solution of the above-mentioned complex catalyst is used for asymmetric epoxidation of various types of enones, depending upon the type of the enone, there may be a case where the yield tends to be low, although a high optical purity will be given to the product. Accordingly, as a method for the reaction, a semi batch method is preferred to a batch method. Further, after adding the above enone to the preliminarily prepared solution of the complex catalyst, CMHP or TBHP is supplied to carry out the reaction, or to the preliminarily prepared catalyst solution, a mixture comprising the above enone and CMHP or TBHP, is supplied to carry out the reaction, whereby it is possible to obtain the desired product in a higher yield.

In the process of the present invention, it is important that the complex catalyst is present in a stabilized condition in the system. For this purpose, the ratio of the oxidizing agent (CMHP or TBHP) present in the system to the lanthanum element becomes important. If the supply rate of the oxidizing agent is slow, and the oxidizing agent in the system becomes deficient, the optical purity of the product tends to be low. On the other hand, if the supply rate of the oxidizing agent is high and an excessive oxidizing agent is present in the system, the yield may decrease. Accordingly, the supply rate of the oxidizing agent is adjusted to the consumption rate of the enone subjected to the reaction. If possible, it is preferred to determine the supply rate of the oxidizing agent after measuring the reaction rate of the enone subjected to the reaction in a reaction system similar to the practical operation.

In the process of the present invention, in a case where (C) the tri(4-fluorophenyl)phosphine oxide, tri(4-chlorophenyl)phosphine oxide or tri(4-trifluoromethylphenyl)phosphine oxide used as a component of a catalyst, the catalyst is more stable than a catalyst that is prepared with a case of triphenylphosphine oxide, so an amount of an excess oxidizing agent in the reaction system does not influence so much a stability of the catalyst as a stability of a catalyst that is prepared with the case of triphenylphosphine oxide. And in a case where (C) the tri(4-trifluorophenyl)phosphine oxide, tri(4-chlorophenyl)phosphine oxide or tri(4-trifluoromethylphenyl)phosphine oxide used as a component of a catalyst, an amount of the catalyst is able to reduce, relative to the substrate to be subjected to the reaction.

In the process of the present invention, in a case where an enone which is slow in the reaction, is subjected to the reaction, it is preferred to employ a method wherein the enone is added to a preliminarily prepared catalyst solution, and then the oxidizing agent is supplied thereto. On the other hand, in a case where an enone which is quick in the reaction such as chalcone, is subjected to the reaction, it is preferred to adopt a method wherein a mixture comprising the enone and the oxidizing agent is supplied to the preliminarily prepared catalyst solution to carry out the reaction.

In the process of the present invention, the reaction temperature varies depending upon the substrate of the enone, but it is usually within a range of from −50° C. to 100° C. As regards the reaction time, usually, the reaction will be completed within 24 hours.

In the process of the present invention, zeolite may be used as the case requires for the purpose of removing water in the system during the preparation of the catalyst or during the reaction, or for the purpose of accelerating the catalyst-forming reaction or the epoxidation reaction.

Such zeolite may be used in any ratio to the enone, but it is usually used in an amount of from 10 mg to 2 g per mmol of the enone. With respect to the type of such zeolite, various zeolites may be employed including type A zeolite represented by molecular sieve 3A, 4A or 5A, molecular sieve 13X, type Y and type L zeolites. Among them, molecular sieve 4A is preferred.

After completion of the reaction, post treatment or purification by e.g. column chromatography may be carried out to obtain the desired optically active epoxide in good yield with a high optical purity.

An asymmetric epoxidation reaction of an enone with high reactivity in good yield and with a high optical purity, is provided by the catalyst of the present invention.

Accordingly, the process of the present invention is very useful as a process for producing an intermediate for various pharmaceuticals or agricultural chemicals.

Now, the present invention will be described in further detail with reference to Examples. However, it should be understood that the present invention is by no means restricted to such specific Examples.

In the following Examples, the optical purities of the products were determined as follows.

Namely, the determination was carried out by using a high performance liquid chromatography having chiral column OB-H or AD of Daicel K. K. mounted, at a flow rate of 1 ml/min of an eluting solvent:

Hexane-$i$-PrOH=2/1–100/1 (vol/vol).

In the case of trans-2,3-epoxy-1,3-diphenylpropan-1-one, when using chiral column OB-H, an eluting solvent: Hexane/i-PrOH=2/1 is supplied at a flow rate of 1 ml/min, peaks of enantiomers of (2S,3R) and (2R,3S) appeared at retention times of 24 minutes and 32 minutes, respectively.

EXAMPLE 1

Into a 50 ml eggplant type flask (A) a magnetic stirrer chip and molecular sieves 4A (70.2 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenyl phosphine oxide (29.3 mg, 0.1053 mmol) and (R)-binaphthol (10.1 mg, 0.0351 mmol) were charged, and the interior of the reaction system was flushed with nitrogen. Then, THF (1 ml) was added, followed by stirring for 5 minutes for dissolution.

Into a separate 50 ml eggplant type flask (B) containing a magnetic stirrer chip, lanthanum triisopropoxide (La(O-iPr)$_3$, 11.1 mg, 0.0351 mmol) was charged, and THF (1 ml) was added thereto, followed by stirring for dissolution. Then, the previously prepared mixture of the eggplant type flask (A) was added to the flask (B) by means of a 2 ml syringe and further rinsed once with THF (1 ml).

The mixture in the flask (B) was held for 1 hour with stirring at room temperature, and then cumene hydroperoxide (166 μl, 1.1234 mmol) was added, followed by further stirring for 30 minutes. 30 minutes later, after visually confirming that the prepared catalyst solution was colored deep green, a solution comprising chalcone (146.2 mg, 0.7022 mmol) and THF (1.7 ml) was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-l-one as colorless transparent oil (amount: 154.3 mg, yield: 98%, optical purity: 99% ee).

EXAMPLE 2

Using the same apparatus for reaction as used in Example 1, a catalyst was prepared in the same manner as in Example 1 except that CMHP was changed to TBHP. The prepared catalyst composition comprised molecular sieves 4A (506 mg), triphenylphosphine oxide (21.2 mg, 0.0758 mmol), (R)-binaphthol (7.2 mg, 0.0251 mmol), lanthanum isopropoxide (La(O-iPr)$_3$, 8.0 mg, 0.0253 mmol), THF (2.52 ml) and a decane solution of TBHP (5M, 0.15 ml, 0.76 mmol).

After confirming that the catalyst solution was colored green, a THF (1 mg) solution of chalcone (105.4 mg, 0.506 mmol) was added, and the reaction was carried out for 30 minutes.

After completion of the reaction, 500 mg of silica gel and 3 mg of methanol were added, followed by stirring for 15 minutes and then by filtration and concentration to obtain a residue, which was purified by a silica gel column (Hexane/AcOEt)=30/1) to obtain trans-(2S,3R)-epoxy-1,3-diphenylpropan-1-one as colorless transparent oil (amount: 112.4 mg, yield: 99%, optical purity: 96% ee).

EXAMPLE 3

Using the same apparatus for reaction as used in Example 1, a catalyst was prepared in the same manner as in Example 1 except that the amount of CMHP was changed to (67.0 µl, 0.567 mmol). For the preparation of the catalyst, 2 hours were spent, and the preparation was carried out with a composition comprising molecular sieves 4A (567 mg), triphenylphosphine oxide (236.6 mg, 0.8502 mmol), (R)-binaphthol (81.1 mg, 0.2834 mmol), lanthanum isopropoxide (La(O-iPr)$_3$, 89.6 mg, 0.2834 mmol), and THF (25.0 ml).

After the preparation of the catalyst, the solution was confirmed to be colored yellowish green, and then a solution comprising chalcone (1180.4 mg, 5.6678 mmol), CMHP (670 µl, 5.6678 mmol) and THF (17.8 ml), was added. After the addition, CMHP (603 µl, 4.081 mmol) was further added, and the reaction was carried out for 1 hour.

After completion of the reaction, post treatment was carried out in the same manner as in Example 1 to obtain trans-(2S,3R)-epoxy-1,3-diphenylpropan-1-one as colorless transparent oil (amount: 1258 mg, yield: 99%, optical purity: 97% ee).

EXAMPLE 4

Using the same apparatus for reaction as used in Example 1, a catalyst was prepared in the same manner as in Example 1 except that the amount of CMHP was changed to (16.2 µl, 0.1097 mmol). For the preparation of the catalyst, 4 hours were spent, and the preparation was carried out with a composition comprising molecular sieves 4A (183 mg), triphenylphosphine oxide (76.3 mg, 0.2742 mmol), (R)-binaphthol (26.2 mg, 0.0914 mmol), lanthanum isopropoxide (La(O-iPr)$_3$, 28.9 mg, 0.0914 mmol), THF (6.0 ml) and CMHP (16.2 µl, 0.1097 mmol).

After preparation of the catalyst, the solution was confirmed to be colored green, and then a solution comprising 1-phenyl-2-buten-1-one (267.3 mg, 1.8281 mmol) instead of chalcone, CMHP (416.0 µl, 2.8154 mmol) and THF (2.6 ml), was added, and the reaction was carried out for 16 hours.

After completion of the reaction, post treatment was carried out in the same manner as in Example 1 to obtain trans-(2S,3R)-epoxy-1-phenylbutan-1-one as colorless transparent oil (amount: 214 mg, yield: 72%, optical purity: 70% ee).

EXAMPLE 5

Using the same apparatus for reaction as used in Example 1, a catalyst was prepared in the same manner as in Example 1 except that the amount of CMHP was changed to (40.5 µl, 0.2741 mmol). For the preparation of the catalyst, 30 minutes were spent, and the preparation was carried out with a composition comprising molecular sieves 4A (137 mg), triphenylphosphine oxide (57.3 mg, 0.2059 mmol), (R)-binaphthol (19.7 mg, 0.0686 mmol), lanthanum isopropoxide (La(O-iPr)$_3$, 21.7 mg, 0.0686 mmol), THF (4.0 ml) and CMHP (40.5 µl, 0.2741 mmol).

After confirming that the catalyst solution was colored green, a solution comprising 4-phenyl-3-buten-2-one (200.0 mg, 1.3681 mmol) instead of chalcone, CMHP (222.0 µl, 1.5024 mmol) and THF (2.4 ml), was added, and the reaction was carried out for 48 hours.

After completion of the reaction, post treatment was carried out in the same manner as in Example 1 to obtain trans-(3S,4R)-epoxy-4-phenylbutan-2-one as colorless transparent oil (amount: 173 mg, yield: 78%, optical purity: 96% ee).

COMPARATIVE EXAMPLE 1

Using the same apparatus for reaction as used in Example 1, a catalyst was prepared with the following composition in the same manner as in Example 1 except that no CMHP was used. Molecular sieves 4A (93.0 mg), triphenylphosphine oxide (38.8 mg, 0.1395 mmol), (R)-binaphthol (13.3 mg, 0.0465 mmol), lanthanum isopropoxide (La(O-iPr)$_3$, 14.7 mg, 0.0465 mmol), and THF (4.2 ml).

The prepared catalyst solution was colored pale yellow. A solution comprising chalcone (193.7 mg, 0.9299 mmol) and THF (2.0 ml), was added thereto, and then CMHP (219.8 µl, 1.4878 mmol) was added, and the reaction was carried out for 1 hour.

After completion of the reaction, post treatment was carried out in the same manner as in Example 1 to obtain trans-(2S,3R)-epoxy-1,3-diphenylpropan-1-one as colorless transparent oil (amount: 208.0 mg, yield: >99.5%, optical purity: 95% ee).

COMPARATIVE EXAMPLE 2

Using the same apparatus for reaction as used in Example 1, a catalyst was prepared with the following composition in the same manner as in Example 1 except that no triphenylphosphine oxide was used. Molecular sieves 4A (96.2 mg), (R)-binaphthol (13.8 mg, 0.0481 mmol), lanthanum isopropoxide (La(O-iPr)$_3$, 15.2 mg, 0.0481 mmol), THF (4.2 ml) and CNHP (113.0 µl, 0.7425 mmol).

The prepared catalyst solution was colorless. A solution comprising chalcone (200.2 mg, 0.9615 mmol) and THF (2.2 ml), was added thereto, and then CMHP (114.3 µl, 0.7510 mmol) was added, and the reaction was carried out for 1 hour, whereupon no product was observed by TLC (thin layer chromatography). Further, the reaction was carried out at room temperature for 23 hours, and then post treatment was carried out in the same manner as in Example 1 to obtain trans-(2S,3R)-epoxy-1,3-diphenylpropan-1-one as colorless transparent oil (amount: 60.4 mg, yield: 28.0%, optical purity: 52% ee).

REFERENCE EXAMPLE 1

Measurement of conversion of trans-4-phenyl-3-buten-2-one

Into a 100 ml eggplant type flask (A), a magnetic stirrer chip and molecular sieves 4A (600 mg, a product preliminarily dried at 180° C. for 4 hours under reduce pressure by means of a vacuum pump) were put and heated and dried by a heat gun for 10 minutes with stirring under reduced pressure by means of a vacuum pump. After cooling to room temperature, triphenylphosphine oxide (264 mg, 0.9489 mmol) and (R)-binaphthol (90.6 mg, 0.3163 mmol) were charged, and the interior of the reaction system was flushed with nitrogen. Then, THF (7 ml) was added, followed by stirring for 5 minutes.

Into a separate 100 ml eggplant type flask (B) containing a magnetic stirrer chip, lanthanum triisopropoxide (La(O-iPr)$_3$, 100 mg, 0.3163 mmol) was introduced and THF (10 ml) was added thereto, followed by stirring for dissolution. Then, the previously prepared mixture of the eggplant type flask (A) was added to the flask (B) by means of a 10 ml syringe and further rinsed once with THF (3 ml).

The mixture in the flask (B) was held for 1 hour with stirring at room temperature, and then cumene hydroperoxide (93 µl, 0.6294 mmol) was added, followed by further stirring for 2 hours.

2 hours later, the prepared catalyst solution was visually confirmed to be colored deep green, and then a solution comprising trans-4-phenyl-3-buten-2-one (PhCH=CHCOMe: 46.2 mg, 0.3163 mmol) and THF (10 ml), was added. Every 1 hour, 1 ml of the reaction mixture was sampled, and 100 ml of silica gel and 100 µl of methanol were added. 30 minutes later, the conversion with time was measured by HPLC having chiral column AD mounted.

From the obtained results, the conversion rate of trans-4-phenyl-3-buten-2-one was 6.5%/hr based on the charged amount.

EXAMPLE 6

Reaction of trans-4-phenyl-3-buten-2-one

Into a 100 ml eggplant type flask (A), a magnetic stirrer chip and molecular sieves 4A (630 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (264 mg, 0.9489 mmol) and (R)-binaphthol (90.6 mg, 0.3163 mmol) were charged, and the interior of the reaction system was flushed with nitrogen. Then, THF (7 ml) was added, followed by stirring for 5 minutes.

Into a separate 100 ml eggplant type flask (B) containing a magnetic stirrer chip, lanthanum triisopropoxide (La(O-iPr)$_3$, 100 mg, 0.3163 mmol) was charged, and THF (10 ml) was added thereto, followed by stirring for dissolution. Then, the previously prepared mixture of the eggplant type flask (A) was addd to the flask (B) by means of a 10 ml syringe and further rinsed once with THF (3 ml).

The mixture in the flask (B) was held for 1 hour with stirring at room temperature. Then, cumene hydroperoxide (100 µl, 0.6768 mmol) was added, followed by stirring for further 2 hours.

2 hours later, the prepared catalyst solution was visually confirmed to be colored deep green, and then a solution comprising trans-4-phenyl-3-buten-2-one (PhCH=CHCOMe: 925 mg, 6.3257 mmol) and THF (10 ml) was added thereto. Then, using a microfeeder, CHHP was supplied at a rate of 60 µl/hr (0.4112 mmol/hr) over a period of 18 hours. For the calculation of the supply rate, it was calculated and set so that the conversion rate became 20 times, since the enone concentration became 20 times as compared with Reference Example 1.

After completion of the dropwise addition, the mixture was further stirred for 2 hours. Then, 500 mg of silica gel and 3 ml of methanol were added, followed by stirring for 15 minutes and then by filtration and concentration to obtain a residue, which was purified by a silica gel column (Hexane/AcOEt=9/1) to obtain trans-(3S,4R)-epoxy-4-phenylbutan-2-one as colorless transparent oil (amount: 974.6 mg, yield: 95%, optical purity: 96% ee).

REFERENCE EXAMPLE 2

Conversion Rate of Trans-Chalcone

Into a 100 ml eggplant type flask (A), a magnetic stirrer chip and molecular sieves 4A (700 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (279.9 mg, 1.0058 mmol) and (R)-binaphthol (96.0 mg, 0.3355 mmol) were charged, and the interior of the reaction system was flushed with nitrogen. Then, THF (10 ml) was added, followed by stirring for 5 minutes.

Into a separate 100 ml eggplant type flask (B) containing a magnetic stirrer chip, lanthanum triisopropoxide (La(O-iPr)$_3$, 106.0 mg, 0.3353 mmol) was charged, and THF (10 ml) was added thereto, followed by stirring for dissolution. Then, the previously prepared mixture of the eggplant type flask (A) was added to the flask (B) by means of a 10 ml syringe and further rinsed once with THF (5 ml).

The mixture in the flask (B) was held for 1 hour with stirring at room temperature. Then, cumene hydroperoxide (74.3 µl, 0.50295 mmol) was added, followed by further stirring for 4 hours.

4 hours later, the prepared catalyst solution was visually confirmed to be colored green, and then a solution comprising trans-chalcone (PhCH=CHCOPh: 69.8 mg, 0.3353 mmol) and THF (15 ml), was added thereto. 1 hour later, 1 ml of the reaction mixture was sampled, and 100 mg of silica gel and 100 µl of methanol were added. 30 minutes later, the conversion was 95% as measured by HPLC having chiral column AD mounted.

EXAMPLE 7

Reaction of Trans-Chalcone

Into a 100 ml eggplant type flask (A), a magnetic stirrer chip and molecular sieves 4A (620 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (259 mg, 0.9299 mmol) and (R)-binaphthol (88.8 mg, 0.3100 mmol) were charged, and the interior of the reaction system was flushed with nitrogen. Then, THF (10 ml) was added, followed by stirring for 5 minutes.

Into a separate 100 ml eggplant type flask (B) containing a magnetic stirrer chip, lanthanum triisopropoxide (La(O-iPr)$_3$, 98.0 mg, 0.3100 mmol) was charged, and THF (15 ml) was added thereto, followed by stirring for dissolution. Then, the previously prepared mixture of the eggplant type flask (A) was added to the flask (B) by means of a 10 ml syringe and further rinsed once with THF (3 ml).

The mixture in the flask (B) was held for 1 hour with stirring at room temperature. Then, cumene hydroperoxide (183 µl, 1.238 mmol) was added, followed by further stirring for 30 minutes.

30 minutes later, the prepared catalyst solution was visually confirmed to be colored green, and then a solution comprising trans-chalcone (PhCH=CHCOPh: 1291.0 mg, 6.1992 mmol), CMHP (916 µl, 6.1992 mmol) and THF (13 ml), was dropwise added thereto over a period of 2 hours by means of a dropping funnel.

After completion of the dropwise addition, stirring was further continued for 1 hour. Then, 500 mg of silica gel and 3 ml of methanol were added, followed by stirring for 15 minutes and then by filtration and concentration to obtain a residue, which was purified by a silica gel column (Hexane/AcOEt=9/1) to obtain trans-(2S,3R)-epoxy-1,3-diphenylpropan-1-one as colorless transparent oil (amount: 1376 mg, yield: 99%, optical purity: >99% ee).

EXAMPLE 8

Reaction of Trans-1-phenyl-2-buten-1-one

Into a 100 ml eggplant type flask (A), a magnetic stirrer chip and molecular sieves 4A (550 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (229.7 mg, 0.8255 mmol) and (R)-binaphthol (78.8 mg, 0.2752 mmol) were charged, and the interior of the reaction system was flushed with nitrogen. Then, THF (6 ml) was added, followed by stirring for 5 minutes.

Into a separate 100 ml eggplant type flask (B) containing a magnetic stirrer chip, lanthanum triisopropoxide (La(O-iPr)$_3$, 87.0 mg, 0.2752 mmol) was charged, and THF (10 ml) was added thereto, followed by stirring for dissolution. Then, the previously prepared mixture of the eggplant type flask (A) was added to the flask (B) by means of a 10 ml syringe and further rinsed once with THF (2 ml).

The mixture in the flask (B) was held for 1 hour with stirring at room temperature. Then, TBHP (5.2 M/decane solution, 63 μl, 0.3302 mmol) was added, followed by further stirring for 1 hour.

1 hour later, the prepared catalyst solution was visually confirmed to be colored yellowish green, and then, a solution comprising trans-1-phenyl-2-buten-1-one (MeCH=CHCOPh: 804.5 mg, 5.5034 mmol), TBHP (5.2 M/decane solution, 1.06 ml, 5.5034 mmol) and THF (8 ml), was dropwise added thereto over a period of 4 hours by means of a dropping funnel. After completion of the dropwise addition, the same TBHP solution (0.25 ml, 1.32076 mmol) was further added. Here, the supply rate was set to be 37%/hr. by the same study as in Reference Examples 1 and 2.

After completion of the dropwise addition, stirring was continued for further 1 hour. Then, 500 mg of silica gel and 3 ml of methanol were added, followed by stirring for 15 minutes and then by filtration and concentration to obtain a residue, which was purified by a silica gel column (Hexane/AcOEt=9/1) to obtain trans-(2S,3R)-epoxy-1,3-diphenylpropan-1-one as colorless transparent oil (amount: 839 mg, yield: 94%, optical purity: 78% ee).

EXAMPLE 9

Reaction of trans-4,4-dimethyl-1-phenyl-1-penten-3-one

Into a 100 ml eggplant type flask (A), a magnetic stirrer chip and molecular sieves 4A (2640 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (1320 mg, 4.7443 mmol) and (R)-binaphthol (452.8 mg, 1.5814 mmol) were charged, and the interior of the reaction system was flushed with nitrogen. Then, THF (25 ml) was added, followed by stirring for 5 minutes.

Into a separate 200 ml eggplant type flask (B) containing a magnetic stirrer chip, lanthanum triisopropoxide (La(O-iPr)$_3$, 500 mg, 1.5814 mmol) was charged, and THF (35 ml) was added thereto, followed by stirring for dissolution. Then, the previously prepared mixture of the eggplant type flask (A) was added to the flask (B) by means of a 20 ml syringe, and further rinsed once with THF (5 ml).

The mixture in the flask (B) was held for 1 hour with stirring at room temperature. Then, cumene hydroperoxide (584 μl, 3.1628 mmol) was added, followed by further stirring for 1.5 hours.

1.5 hours later, the prepared catalyst solution was visually confirmed to be colored deep green, and then a solution comprising trans-4,4-dimethyl-1-phenyl-1-penten-3-one (PhCH=CHCOtBu: 9925 mg, 52.7144 mmol) and THF (35 ml), was added thereto, and then using a dropping funnel, CMHP was supplied at a rate of 671 μl/hr (3.63 mmol/hr) over a period of 18 hours.

Here, the supply rate was calculated from the result (6.0%/hr) of the conversion rate obtained in the same manner as in Reference Example 1.

After completion of the dropwise addition, stirring was continued for further 2 hours. Then, 5 g of silica gel and 50 ml of methanol were added, followed by stirring for 30 minutes and then by filtration and concentration to obtain a residue, which was purified by a silica gal column (Hexane/AcOEt=9/1) to obtain trans-4-epoxy-2,2-dimethyl-5-phenyl-4-pentan-3-one as white crystals (amount: 10.23 g, yield: 95%, optical purity: >99% ee).

In the following Examples, the determination of the optical purities of the products was carried out as follows.

Namely, the measurement of trans-(2S,3R)-epoxy-1,3-diphenylpropan-1-one was carried out by a high performance liquid chromatography having chiral column OB-H of Daicel K. K. mounted, at a flow rate of 1 ml/min of an eluting solvent: Hexane/i-PrOH=90/10 (vol/vol).

EXAMPLE 10

Into a 50 ml eggplant type flask (A), a magnetic stirrer chip and molecular sieves 4A (128 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, tri(4-fluorophenyl)phosphine oxide (63.1 mg, 0.1898 mmol) and (R)-binaphthol (18.1 mg, 0.0633 mmol) were charged, and the interior of the reaction system was flushed with nitrogen. Then, THF (2.5 ml) was added, followed by stirring for 5 minutes for dissolution.

Into a separate 50 ml eggplant type flask (B) containing a magnetic stirrer chip, lanthanum triisopropoxide (La(O-iPr)$_3$, 20.0 mg, 0.0633 mmol) was charged, and THF (2.0 ml) was added thereto, followed by stirring for dissolution. Then, the previously prepared mixture of the eggplant type flask (A) was added to the flask (B) by means of a 2 ml syringe and further rinsed once with THF (0.6 ml).

The mixture in the flask (B) was held for 1 hour with stirring at room temperature. Then, cumene hydroperoxide (299 μl, 2.024 mmol) was added, followed by further stirring for 5 hours.

5 hours later, the prepared catalyst solution was visually confirmed to be colored deep green, and then, a solution comprising chalcone (263.4 mg, 1.2651 mmol) and THF (2.5 ml) was added, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 245.7 mg, yield: 86.6%, optical purity: 98.9% ee).

EXAMPLE 11

Into a 50 ml eggplant type flask (A), a magnetic stirrer chip and molecular sieves 4A (146 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, tri(4-chlorophenyl)phosphine oxide (83.3 mg, 0.2182 mmol) and (R)-binaphthol (20.8 mg, 0.0727 mmol) were charged, and the interior of the reaction system was flushed with nitrogen. Then, THF (3.0 ml) was added, followed by stirring for 5 minutes for dissolution.

Into a separate 50 ml eggplant type flask (B) containing a magnetic stirrer chip, lanthanum triisopropoxide (La(O-iPr)$_3$, 23.0 mg, 0.0727 mmol) was charged, and THF (2.0 ml) was added thereto, followed by stirring for dissolution. Then, the previously prepared mixture of the eggplant type flask (A) was added to the flask (B) by means of a 2 ml syringe and further rinsed once with THF (1.0 ml).

The mixture in the flask (B) was held for 1 hour with stirring at room temperature. Then, cumene hydroperoxide (344 µl, 2.3279 mmol) was added, followed by stirring for further 5 hours.

5 hours later, the prepared catalyst solution was visually confirmed to be colored deep green, and then, a solution comprising chalcone (303.0 mg, 1.4549 mmol) and THF (2.8 ml), was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 252.5 mg, yield: 77.4%, optical purity: 98.9% ee).

EXAMPLE 12

Into a 50 ml eggplant type flask (A), a magnetic stirrer chip and molecular sieves 4A (133 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, tri(4-trifluoromethylphenyl)phosphine oxide (96.1 mg, 0.1993 mmol) and (R)-binaphthol (19.0 mg, 0.0664 mmol) were charged, and the interior of the reaction system was flushed with nitrogen. Then, THF (3.0 ml) was added, followed by stirring for 5 minutes for dissolution.

Into a separate 50 ml eggplant type flask (B) containing a magnetic stirrer chip, lanthanum triisopropoxide (La(O-iPr)$_3$, 21.0 mg, 0.0664 mmol) was charged, and THF (2.0 ml) was added thereto, followed by stirring for dissolution. Then, the previously prepared mixture of the eggplant type flask (A) was added to the flask (B) by means of a 2 ml syringe and further rinsed once with THF (1.0 ml).

The mixture in the flask (B) was held for 1 hour with stirring at room temperature. Then, cumene hydroperoxide (314 µl, 2.1254 mmol) was added, followed by stirring for further 5 hours.

5 hours later, the prepared catalyst solution was visually confirmed to be colored deep green, and then a solution comprising chalcone (276.6 mg, 1.3284 mmol) and THF (2.0 ml), was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 223.8 mg, yield: 75.1%, optical purity: 95.3% ee).

COMPARATIVE EXAMPLE 3

Into a 50 ml eggplant type flask (A), a magnetic stirrer chip and molecular sieves 4A (146 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (60.7 mg, 0.2182 mmol) and (R)-binaphthol (20.8 mg, 0.0727 mmol) were charged, and the interior of the reaction system was flushed with nitrogen. Then, THF (3.0 ml) was added, followed by stirring for 5 minutes for dissolution.

Into a separate 50 ml eggplant type flask (B) containing a magnetic stirrer chip, lanthanum triisopropoxide (La(O-iPr)$_3$, 23.0 mg, 0.0727 mmol) was charged, and THF (2.0 ml) was added thereto, followed by stirring for dissolution. Then, the previously prepared mixture of the eggplant type flask (A) was added to the flask (B) by means of a 2 ml syringe and further rinsed once with THF (1.0 ml).

The mixture in the flask (B) was held for 1 hour with stirring at room temperature. Then, cumene hydroperoxide (344 µl, 2.3279 mmol) was added, followed by stirring for further 5 hours.

5 hours later, the prepared catalyst solution was visually confirmed to be colored blackish green, and then a solution comprising chalcone (303.0 mg, 1.4549 mmol) and THF (2.8 ml), was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 134.1 mg, yield: 41.1%, optical purity: 94.5% ee).

Further, 166.7 mg of an unreacted material was recovered (recovery rate: 55.0%).

EXAMPLE 13

Into a 50 ml eggplant type flask (A), a magnetic stirrer chip and molecular sieves 4A (1330 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, tri(4-fluorophenyl)phosphine oxide (66.2 mg, 0.1993 mmol) and (R)-binaphthol (19.0 mg, 0.0664 mmol) were charged, and the interior of the reaction system was flushed with nitrogen. Then, THF (25 ml) was added, followed by stirring for 5 minutes for dissolution.

Into a separate 100 ml eggplant type flask (B) containing a magnetic stirrer chip, lanthanum triisopropoxide (La(O-iPr)$_3$, 21.0 mg, 0.0664 mmol) was charged, and THF (20 ml) was added thereto, followed by stirring for dissolution. Then, the previously prepared mixture of the eggplant type flask (A) was added to the flask (B) by means of a 20 ml syringe and further rinsed once with THF (10 ml).

The mixture in the flask (B) was held for 1 hour with stirring at room temperature. Then, cumene hydroperoxide (3141 μl, 21.2544 mmol) was added, followed by stirring for further 30 minutes.

30 minutes later, the prepared catalyst solution was visually confirmed to be colored deep green, and a solution comprising chalcone (2767 mg, 13.2840 mmol) and THF (25 ml), was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 2920 mg, yield: 98.0%, optical purity: 98.0% ee).

COMPARATIVE EXAMPLE 4

Into a 50 ml eggplant type flask (A), a magnetic stirrer chip and molecular sieves 4A (1520 mg, a product preliminarily dried at 180° C. for 4 hours under reduced pressure by means of a vacuum pump) were put and heated and dried by a heat gun for 10 minutes with stirring under reduced pressure by means of a vacuum pump. After cooling to room temperature, triphenylphosphine oxide (63.4 mg, 0.2277 mmol) and (R)-binaphthol (21.7 mg, 0.0759 mmol) were charged, and the interior of the reaction system was flushed with nitrogen. Then, THF (30 ml) was added, followed by stirring for 5 minutes for dissolution.

Into a separate 100 ml eggplant type flask (B) containing a magnetic stirrer chip, lanthanum triisopropoxide (La(O-iPr)$_3$, 24.0 mg, 0.0759 mmol) was charged, and THF (25 ml) was added thereto, followed by stirring for dissolution. Then, the previously prepared mixture of the eggplant type flask (A) was added to the flask (B) by means of a 20 ml syringe and further rinsed once with THF (6.5 ml).

The mixture in the flask (B) was held for 1 hour with stirring at room temperature. Then, cumene hydroperoxide (3589 μl, 24.2908 mmol) was added, followed by stirring for further 30 minutes.

30 minutes later, the prepared catalyst solution was visually confirmed to be colored green, and a solution comprising chalcone (3162 mg, 15.1817 mmol) and THF (30 ml), was added thereto, and the reaction was carried out for 1 hour.

After completion of the reaction, 500 mg of silica gel and 3 ml of methanol were added, followed by stirring for 15 minutes and then by filtration and concentration to obtain a residue, which was purified by a silica gel column (Hexane/AcOEt=30/1) to obtain trans-(2S,3R)-epoxy-1,3-diphenylpropan-1-one as colorless transparent oil (amount: 2622 mg, yield: 77.0%, optical purity: 98.0% ee).

Further, by thin layer chromatography, remaining of the starting material was confirmed.

The entire disclosure of Japanese Patent Application Nos. 2000-052148 filed on Feb. 23, 2000 and 2000-073996 filed on Mar. 13, 2000 including specification, claims, drawings and summary are incorporated herein by reference in its entirety.

What is claimed is:

1. A process for producing an optically active epoxide of the following formula (2):

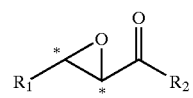

(2)

wherein each of $R_1$ and $R_2$ which are independent of each other, is a $C_{1-20}$ linear, branched or cyclic alkyl group, an aromatic group, an aromatic group substituted by from 1 to 5 $C_{1-5}$ alkyl groups, an aromatic group substituted by from 1 to 5 $C_{1-5}$ alkoxy groups, an aromatic group substituted by from 1 to 5 halogen atoms, a $C_{1-5}$ linear, branched or cyclic alkyl group substituted by an aromatic group, or a $C_{1-5}$ linear, branched or cyclic alkyl group substituted by a halogenated aromatic group, and symbol * represents optically active carbon, which comprises reacting an enone of the following formula (1)

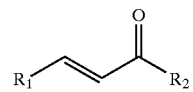

(1)

wherein $R_1$ and $R_2$ are as defined above, with an oxidizing agent in the presence of a complex catalyst produced by a process comprising the steps of (1) adding to a solvent (A) an optically active binaphthol. (B) lanthanum triisopropoxide, (C) triphenylphosphine oxide, and (D) cumene hydroperoxide or tert-butyl hydroperoxide present in an amount of from 1 to 10 mols per mol of (B) lanthanum triisopropoxide to form a solution and (2) reacting the solution of step (1) until a complex catalyst is formed and dissolved as indicated by a yellow-green to green color.

2. The process for producing an optically active epoxide according to claim 1, wherein the reaction is carried out by adding the enone to a catalyst solution and then supplying cumene hydroperoxide or tert-butyl hydroperoxide thereto.

3. The process for producing an optically active epoxide according to claim 1, wherein the reaction is carried out by supplying a mixture comprising the enone and cumene hydroperoxide or tert-butyl hydroperoxide to a catalyst solution.

4. A process for producing an optically active epoxide of the following formula (2)

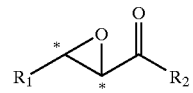

(2)

wherein each of $R_1$ and $R_2$ which are independent of each other, is a $C_{1-20}$ linear, branched or cyclic alkyl group, an aromatic group, an aromatic group substituted by from 1 to 5 $C_{1-5}$ alkyl groups, an aromatic group substituted by from 1 to 5 $C_{1-5}$ alkoxy groups, an aromatic group substituted by from 1 to 5 halogen atoms, a $C_{1-5}$ linear, branched or cyclic alkyl group substituted by an aromatic group, or a $C_{1-5}$ linear, branched or cyclic alkyl group substituted by a halogenated aromatic group, and symbol * represents optically active carbon, which comprises reacting an enone of the following formula (1):

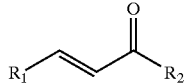
(1)

wherein $R_1$ and $R_2$ are as defined above, with an oxidizing agent in the presence of a catalyst produced by a process comprising the steps of
(1) adding to a solvent: (A) an optically active binaphthol, (B) lanthanum triisopropoxide, and (C) tri (4-fluorophenyl) phosphine oxide, tri (4-chlorophenyl) phosphine oxide or tri (4-trifluoromethylphenyl) phosphine oxide to form a solution and
(2) reacting the solution of step (1) until a complex catalyst is formed and dissolved as indicated by a yellow-green to green color.

* * * * *